United States Patent [19]

Manis et al.

[11] Patent Number: 4,644,074

[45] Date of Patent: Feb. 17, 1987

[54] STABILIZED ORGANOPOLYSILOXANES AND A PROCESS FOR STABILIZING THE SAME

[75] Inventors: Paul A. Manis, Allentown, Pa.; Eugene R. Martin, Onsted; Ronald L. Muntz, Adrian, both of Mich.

[73] Assignee: SWS Silicones Corporation, Adrian, Mich.

[21] Appl. No.: 721,746

[22] Filed: Apr. 10, 1985

[51] Int. Cl.⁴ .............................. C07F 7/08; C07F 7/10
[52] U.S. Cl. ................................................ 556/401
[58] Field of Search ......................................... 556/401

[56] References Cited

U.S. PATENT DOCUMENTS

| | | | |
|---|---|---|---|
| 2,389,803 | 11/1945 | McGregor et al. | 556/401 |
| 2,389,805 | 11/1945 | McGregor et al. | 556/401 |
| 2,389,807 | 11/1945 | McGregor et al. | 556/401 |
| 3,078,229 | 2/1963 | Cox | 556/401 X |
| 3,883,628 | 5/1975 | Martin | 264/54 |
| 4,078,104 | 3/1978 | Martin | 427/387 |
| 4,203,413 | 5/1980 | Burkhardt et al. | 556/401 |
| 4,230,632 | 10/1980 | Chapman | 556/401 |

Primary Examiner—Paul F. Shaver

[57] ABSTRACT

Organopolysiloxane fluids are stabilized against degradation in the presence of kaolin clays at elevated temperatures by adding an amine containing compound to the organopolysiloxane fluids.

23 Claims, No Drawings

STABILIZED ORGANOPOLYSILOXANES AND A PROCESS FOR STABILIZING THE SAME

The present invention relates to organopolysiloxanes which are resistant to kaolin clay induced degradation and more particularly to a process for stabilizing organopolysiloxane fluids against degradation in the presence of kaolin clays at elevated temperatures.

BACKGROUND OF THE INVENTION

Heretofore, organopolysiloxanes have been known to equilibrate in the presence of acidic clays to form volatile, lower molecular weight siloxanes. This often results in the loss of desired properties and the formation of volatile, low molecular weight siloxanes and cyclosiloxanes.

The organopolysiloxane fluids have been used in electrostatic copying apparatus as a release agent to effect release between the toner treated paper and a heated fuser roll. The toner treated paper generally contains kaolin clay and when the paper contacts the release agent, paper residue containing kaolin clay is collected along with excess release agent in a reservoir. When the reservoir contents are reused, the combination of acidic kaolin clay and the high temperature of the fuser roll causes the organopolysiloxane fluids to degrade to volatile, low molecular weight siloxanes. Condensation of the low molecular weight volatile siloxanes on electrical switches will inhibit the switches function due to the good dielectric properties of the siloxanes.

Therefore, it is an object of this invention to provide a process for stabilizing organopolysiloxanes. Another object of this invention is to provide a process for stabilizing organopolysiloxanes against degradation in the presence of kaolin clays. A further object of this invention is to provide a process where organopolysiloxane fluids are rendered resistant to degradation in the presence of heat and kaolin clay without significantly affecting the properties of the organopolysiloxanes.

SUMMARY OF THE INVENTION

The foregoing objects and others which will become apparent from the following description are accomplished in accordance with this invention, generally speaking, by providing stabilized organopolysiloxanes which comprises adding an amine containing compound to an organopolysiloxane fluid at a temperature of from about 20° C. to 200° C. The resultant composition is resistant to degradation in the presence of kaolin clays even at elevated temperatures.

DETAILED DESCRIPTION OF THE INVENTION

Organopolysiloxane fluids which are stabilized in accordance with this invention have recurring units of the general formula

where the R(s), which may be the same or different, represent monovalent hydrocarbon radicals having from 1 to 18 carbon atoms or halogenated monovalent hydrocarbon radicals having from 1 to 18 carbon atoms and X is a number equal to at least 2.

Suitable examples of monovalent hydrocarbon radicals represented by R are alkyl radicals, such as the methyl, ethyl, propyl, butyl, octyl, dodecyl, and octadecyl radicals; aryl radicals, such as the phenyl and naphthyl radicals; alkenyl radicals, such as the vinyl and allyl radicals; cycloalkyl radicals, such as the cyclobutyl, cyclopentyl and cyclohexyl radicals; alkaryl radicals, such as the tolyl, xylyl, ethylphenyl radicals; aralkyl radicals, such as the benzyl, α-phenylethyl, B-phenylethyl and α-phenylbutyl radicals.

Examples of halogenated monovalent hydrocarbon radicals are the haloalkyl radicals such as the 3,3,3-trifluoropropyl radical and halaryl radicals such as the o-, m-, p-chlorophenyl radicals.

Any linear, branched or cyclic organopolysiloxanes having an average of from 1.75 to 2.25 organic radicals per silicon atom may be employed. It is preferred that the polyorganosiloxanes have a viscosity of between about 5 and 1,000,000 mPa.s at 25° C. and more preferably between about 50 and 300,000 mPa.s at 25° C. Also, it is possible to combine high and low viscosity fluids to form a fluid having the desired viscosity.

Examples of suitable organopolysiloxanes are trialkylsiloxy-endblocked diorganopolysiloxanes such as trimethylsiloxy-endblocked dimethylpolysiloxanes, triethylsiloxy endblocked-diethylpolysiloxanes; alkenyl terminated diorganopolysiloxanes such as vinyl-endblocked dimethylpolysiloxanes, diethylpolysiloxanes, dipropylpolysiloxanes and copolymers having dimethylsiloxane units and diphenyl siloxane units or methylphenyl siloxane units and dimethylsiloxane units. Preferably, the organopolysiloxanes are trimethylsiloxy-endblocked dimethylpolysiloxanes.

Amine containing compounds which may be employed as stabilizing agents are organic amines having the general formula

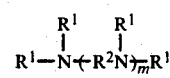

and amine containing silicon compounds such as silanes of the general formula

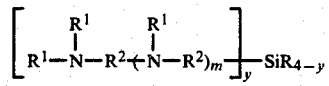

and siloxanes of the general formula

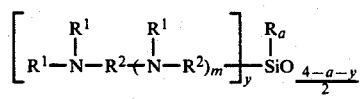

where R is the same as above, R¹ which may be the same or different represents hydrogen or monovalent hydrocarbon radicals having from 1 to 30 carbon atoms which may be substituted with hydroxyl groups, R², which is the same or different, is a divalent hydrocarbon radical having from 1 to 20 carbon atoms, a is a number of from 0 to 2, m is an integer of from 0 to 20 and y is a number of from 1 to 4.

Examples of monovalent hydrocarbon radicals represented by R¹ are alkyl radicals such as the methyl, ethyl, propyl, butyl, hexyl, octyl, decyl, dodecyl, hexadecyl, octadecyl, eicosyl, docosyl, hexacosyl, octacosyl and triacontyl radicals; alkenyl radicals such as ethenyl, 1-propenyl, 1-isobutenyl, 1-pentyl, 1-hexenyl, 3,3-dimethyl-1-butenyl and the various isomers of heptenyl, octenyl, nonenyl, dodecenyl, heptadecenyl, nondecenyl and eicosenyl; aryl radicals such as phenyl, α-naphthyl, B-naphthyl and α-anthryl radicals; alkaryl radicals such as the o-tolyl, m-tolyl, 2,3-xylyl, 2,4-xylyl, o-cumenyl, m-cumenyl, o-ethylphenyl, p-ethylphenyl, 2-methyl-α-naphthyl, 1-ethyl-B-naphthyl, 2,3-dipropyl-α-naphthyl radicals and aralkyl radicals such as the benzyl, α-phenylethyl, B-phenylethyl, 2-phenylbutyl, α'-naphthyl-methyl, α-(α'-naphthyl)-ethyl and the corresponding α' and B' naphthyl derivatives of n-amyl up to and including the octadecyl radical.

Examples of divalent hydrocarbon radicals represented by $R^2$ are alkylene radicals such as ethylene, trimethylene, tetramethylene, hexamethylene, octamethylene, tetradecamethylene, octadecamethylene and arylene radicals such as phenylene diphenylene and naphthylene radicals.

Examples of suitable organic amines which may be employed are aliphatic and aromatic, primary, secondary and tertiary amines such as isopropylamine, n-propylamine, butylamine, sec-butylamine, tert-butylamine, N-methyl-N-ethylamine, N-methyl-N-ethylisopropylamine, 2-amino-3-methylbutane, N,N-dimethylethylamine, allylamine, n-amylamine, isoamylamine, n-hexylamine, n-octylamine, n-decylamine, N,N-diethylpropylamine, ethanolamine, diethanolamine, triethanolamine, ethylenediamine, diethylenetriamine, triethylenetetramine, aniline, methylaniline, dimethylaniline, ethylaniline, o, m or p- toluidine, 2,3-dimethylaniline, 3,5-dimethylaniline, 2,4-dimethylaniline, diphenylamine, triphenylamine, p-phenylenediamine and 4,4' diaminodiphenylmethane.

Other amines which may be employed as those having the formulas $$CH_3(CH_2)_{16}CH_2\overset{H}{\underset{}{N}}CH_3, CH_3(CH_2)_{16}CH_2N(CH_3)_2,$$

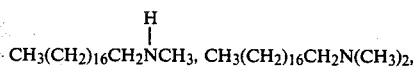

and

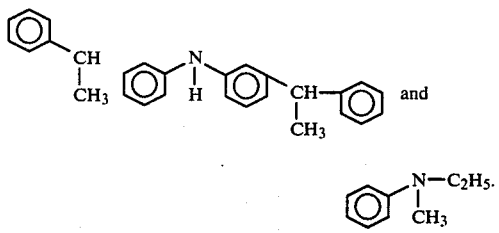

Suitable examples of amine containing silicon compounds which may be used in the process of this invention are amino-functional silanes such as beta-aminopropyltriethoxysilane, gamma-aminopropyltrimethoxysilane, methyl-beta-D(aminoethyl)-gamma-aminopropyldimethoxysilane, omega-aminohexyltributoxysilane, beta-(aminoethyl)propyltrimethoxysilane, beta-(aminoethyl)hexyltriethoxysilane, beta-(aminopropyl)-butyltributoxysilane, (trimethylsilylpropyl)ethylenediamine, (trimethylsilylisobutyl)-ethylenediamine.

The aminofunctional siloxanes employed in the process of this invention are well known in the art. They may be prepared in accordance with the process described in U.S. Pat. No. 2,947,771 to Bailey, in which an aminofunctional silane is equilibrated with a siloxane in the presence of an alkali-metal hydroxide. Also, they may be prepared in accordance with the process described in U.S. Pat. No. 3,598,853 to Friedman et al, in which an aminofunctional silane is condensed with a silanol terminated polydiorganosiloxane. Other methods for preparing aminofunctional siloxane fluids are described in U.S. Pat. Nos. 3,890,269 to Martin; 3,930,809 to Jex et al and 3,045,036 to Jex et al. The aminofunctional siloxanes described in these references and their methods of preparation are incorporated herein by reference.

Representative examples of aminofunctional siloxanes are

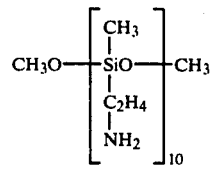

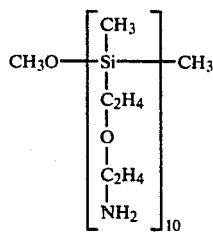

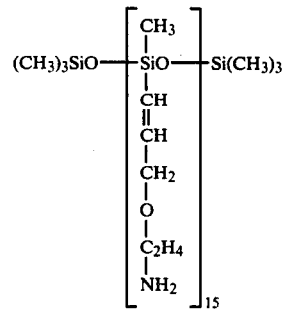

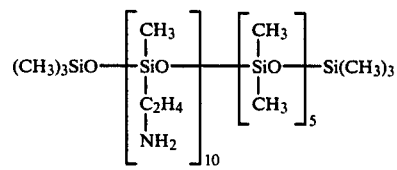

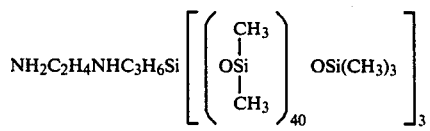

and the like.

The amount of amine containing compound which may be added to the organopolysiloxane fluid to prevent degradation in the presence of kaolin clays may range from about 0.001 up to about 5 percent by weight and more preferably from about 0.01 up to about 2 percent by weight based on the weight of the organopolysiloxane fluid and the amine containing compound.

It is preferred that the amine containing compound be added to the organopolysiloxane at a temperature of from about 20° C. to 40° C and then heated up to a temperature of about 80° C. and more preferably from about 60° to 80° C. However, it has been found that the organopolysiloxanes may be stabilized in the absence of heat by merely mixing the amine with the organopolysiloxanes at temperatures as low as 20° C.

The organopolysiloxanes obtained from the process of this invention are stable at elevated temperatures in the presence of kaolin clays. These organopolysiloxanes may be used in an electrostatic printing apparatus where they contact kaolin clay impregnated paper without gelling even at elevated temperatures.

Specific embodiments of this invention are further illustrated in the following examples in which all parts are by weight unless otherwise specified.

EXAMPLE 1

About 99.95 parts of a trimethylsiloxy-endblocked dimethylpolysiloxane having a viscosity of 350 mPa.s at 25° C. are mixed with 0.05 parts of 4,4'-bis-(alpha-methylbenzyl)diphenylamine of the formula

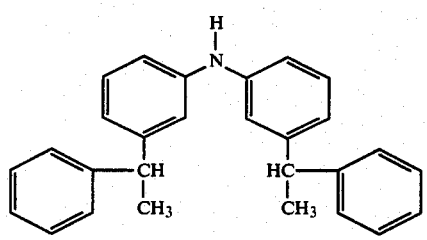

at a temperature of from 20° to 30° C. About five parts of the mixture are placed in two aluminum evaporating dishes. To one dish is added 0.1 part of kaolin clay (available from R. T. Vanderbilt Co.), and then both dishes are placed in a 200° C. forced air oven for 24 hours. The percent of weight loss is determined. The results are illustrated in Table I.

EXAMPLE 2

The procedure of Example 1 is repeated except that 99.5 parts of a trimethylsiloxy-endblocked dimethylpolysiloxane fluid having a viscosity of 350 mPa.s at 25° C. and 0.5 parts of the amine are used. The results are shown in Table I.

COMPARISON EXAMPLE V₁

The procedure of Example 1 is repeated except that the amine is omitted. The results are shown in Table I.

TABLE I

| Example No. | Siloxane Fluid (Parts) | Amine Compound | Amine Compound (Parts) | (Percent) Weight Loss | |
|---|---|---|---|---|---|
| | | | | Without Kaolin Clay | With Kaolin Clay |
| 1 | 99.95 | BDPA | .05 | 0.15 | 1.18 |
| 2 | 99.5 | BDPA | .5 | 0.32 | 0.45 |
| Comparison Example V₁ | 100 | — | — | 0.17 | 57.3 |

BDPA = 4,4'-bis-(alpha-methylbenzyl)diphenylamine

EXAMPLES 2 to 19

The procedure of Example 1 is repeated in the following examples, except that other amines are substituted for 4,4'-bis-(alpha-methylbenzyl)diphenylamine of Example 1. The results are shown in Table II.

TABLE II

| Example No. | Siloxane Fluid* (Parts) | Amine Compound | Amine Compound (Parts) | (Percent) Weight Loss | |
|---|---|---|---|---|---|
| | | | | Without Kaolin Clay | With Kaolin Clay |
| 3 | 99.90 | diphenylamine | 0.10 | 0.27 | 0.128 |
| 4 | 99.0 | diphenylamine | 1.0 | 1.17 | 1.23 |
| 5 | 99.95 | 3-aminopropyltriethoxysilane | 0.05 | .17 | 12.52 |
| 6 | 99.90 | 3-aminopropyltriethoxysilane | 0.10 | .23 | 2.31 |
| 7 | 99.0 | 3-aminopropyltriethoxysilane | 1.0 | .86 | 1.2 |
| 8 | 99.95 | 2-aminoethyl-3-propyltrimethoxysilane | 0.05 | .13 | 36.24 |
| 9 | 99.9 | 2-aminoethyl-3-propyltrimethoxysilane | 0.10 | .16 | 26.76 |
| 10 | 99.0 | 2-aminoethyl-3-propyltrimethoxysilane | 1.0 | .97 | 1.17 |
| 11 | 99.95 | dimethyloctadecylamine | 0.05 | .21 | 2.22 |
| 12 | 99.9 | dimethyloctadecylamine | 0.10 | .28 | .70 |
| 13 | 99.0 | dimethyloctadecylamine | 1.0 | 1.13 | 1.12 |
| 14 | 99.95 | N—methyloctadecylamine | 0.05 | .19 | 1.37 |
| 15 | 99.9 | N—methyloctadecylamine | 0.10 | .24 | 1.07 |
| 16 | 99.0 | N—methyloctadecylamine | 1.0 | 1.02 | 1.03 |
| 17 | 99.95 | octadecylamine | 0.05 | 0.17 | 2.41 |
| 18 | 99.9 | octadecylamine | 0.10 | 0.26 | 1.05 |
| 19 | 99.0 | octadecylamine | 1.0 | 0.92 | 0.99 |
| Comparison Example V₁ | 100 | — | — | 0.17 | 57.3 |

*trimethylsiloxy-endblocked polydimethylsiloxane (viscosity — 350 mPa.s at 25° C.)

EXAMPLE 20

The procedure of Example 1 is repeated, except that 4 parts of beta-aminopropyltrimethylsilane is added to 99 parts of a trimethylsiloxy-endblocked polydimethylsiloxane and heated to 40° C. The resultant product exhibits improved stability in the presence of kaolin clay at an elevated temperature.

EXAMPLE 21

The procedure of Example 20 is repeated, except that 3 parts of (trimethylsilylpropyl)ethylenediamine is substituted for the beta-aminopropyltrimethylsilane. The resultant composition exhibits improved stability in the presence of kaolin clay.

EXAMPLE 22

The procedure of Example 1 is repeated, except that a vinyl endblocked polydimethylsiloxane is substituted for the trimethylsiloxy-endblocked polydimethylsiloxane. The resultant composition exhibits improved stability in the presence of kaolin clay.

EXAMPLE 23

The procedure of Example 1 is repeated, except that 1 part of an aminofunctional polysiloxane having the formula

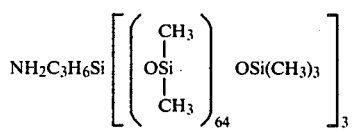

is substituted for the 4,4'-bis-(alpha-methylbenzyl)diphenylamine. The results are shown in Table III.

TABLE III

| Example No. | Siloxane Fluid (Parts) | Amine Compound | Amine Compound (Parts) | (Percent) Weight Loss Without Kaolin Clay | With Kaolin Clay |
|---|---|---|---|---|---|
| 23 | 96.5 | AF | 3.5 | 0.44 | 9.55 |
| Comparison Example V₁ | 100 | — | — | 0.17 | 57.3 |

AF = Aminofunctional fluid

What is claimed is:

1. A composition containing an organopolysiloxane fluid, kaolin clay and from 0.001 up to 5 percent by weight of an amine containing compound based on the weight of the organopolysiloxane fluid and the amine containing compound.

2. The composition of claim 1, wherein the amine containing compound has the formula

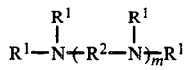

where $R^1$ is selected from the group consisting of hydrogen, monovalent hydrocarbon radicals having from 1 to 30 carbon atoms and monovalent hydrocarbon radicals substituted with hydroxyl groups, $R^2$ is a divalent hydrocarbon radical having from 1 to 20 carbon atoms and m is an integer of from 0 to 20.

3. The composition of claim 1, wherein the amine containing compound is an aminofunctional silane.

4. The composition of claim 3, wherein aminofunctional silane has the formula

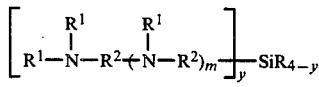

Where R is selected from the group consisting of a monovalent hydrocarbon radical having from 1 to 18 carbon atoms and a halogenated monovalent hydrocarbon radical having from 1 to 18 carbon atoms, $R^1$ is selected from the group consisting of hydrogen, monovalent hydrocarbon radicals having from 1 to 30 carbon atoms and monovalent hydrocarbon radicals substituted with hydroxyl groups, $R^2$ is a divalent hydrocarbon radical having from 1 to 20 carbon atoms, m is an integer of from 0 to 20 and y is a number of from 1 to 4.

5. A process for stabilizing an organopolysiloxane fluid against degradation in the presence of kaolin clay which comprises adding to the organopolysiloxane fluid an amine containing compound in an amount of from 0.001 up to 5 percent by weight based on the weight of the amine containing compound and the organopolysiloxane fluid.

6. The process of claim 5, wherein the amine containing compound has the formula

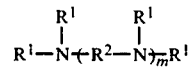

where $R^1$ is selected from the group consisting of hydrogen, monovalent hydrocarbon radicals having from 1 to 30 carbon atoms and monovalent hydrocarbon radicals substituted with hydroxyl groups, $R^2$ is a divalent hydrocarbon radical having from 1 to 20 carbon atoms and m is an integer of from 0 to 20.

7. The composition of claim 3, wherein the aminofunctional silane is 3-aminopropyltriethoxysilane.

8. The composition of claim 3, wherein the aminofunctional silane is 2-aminoethyl-3aminopropyltrimethoxysilane.

9. The process of claim 5, wherein $R^1$ is substituted with a hydroxyl group.

10. The process of claim 5, wherein the mixture containing the organopolysiloxane fluid and amine containing compound is heated to a temperature up to 200° C.

11. The process of claim 5, wherein the organopolysiloxane fluid has recurring units of the formula $(R_2SiO)_x$ where R is selected from the group consisting of monovalent hydrocarbon radicals and halogenated monovalent hydrocarbon radicals and x is a number equal to at least 2.

12. The process of claim 5, wherein the organopolysiloxane fluid has an average of from 1.75 to 2.25 organic radicals per silicon atom.

13. The process of claim 5, wherein the organopolysiloxane fluid is a trimethylsilyloxy-endblocked dimethylpolysiloxane fluid.

14. The process of claim 5, wherein the aminofunctional silane is 3-aminopropyltriethoxysilane.

15. The process of claim 5, wherein the aminofunctional silane is 2-aminoethyl-3-aminopropyltrimethoxysilane.

16. The process of claim 5, wherein the amine containing compound is present in an amount of from 0.1 to 2 percent by weight based on the weight of the organopolysiloxane fluid and the amine containing compound.

17. The process of claim 5, wherein the amine containing compound is present in an amount of about 1 percent by weight based on the weight of the organopolysiloxane fluid and the amine containing compound.

18. The composition of claim 1, wherein the amine containing compound is an aminofunctional siloxane.

19. The composition of claim 18, wherein the aminofunctional siloxane has the formula

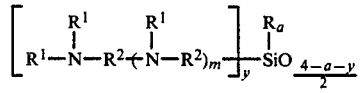

where R is selected from the group consisting of a monovalent hydrocarbon radical having from 1 to 18 carbon atoms and a halogenated monovalent hydrocarbon radical having from 1 to 18 carbon atoms, $R^1$ is selected from the group consisting of hydrogen, monovalent hydrocarbon radicals having from 1 to 30 carbon atoms and monovalent hydrocarbon radicals substituted with hydroxyl groups, $R^2$ is a divalent hydrocarbon radical having from 1 to 20 carbon atoms, a is a number of from 0 to 2, m is an integer of from 0 to 20 and y is a number of from 1 to 4.

20. The process of claim 5, wherein the amine containing compound is an aminofunctional silane.

21. The process of claim 20, wherein the aminofunctional silane has the formula

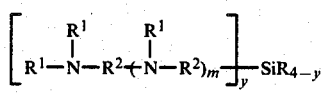

where R is selected from the group consisting of a monovalent hydrocarbon radical having from 1 to 18 carbon atoms and a halogenated monovalent hydrocarbon radical having from 1 to 18 carbon atoms, $R^1$ is selected from the group consisting of hydrogen, monovalent hydrocarbon radicals having from 1 to 30 carbon atoms and monovalent hydrocarbon radicals substituted with hydroxyl groups, $R^2$ is a divalent hydrocarbon radical having from 1 to 20 carbon atoms, m is an integer of from 0 to 20 and y is a number of from 1 to 4.

22. The process of claim 5, wherein the amine containing compound is an aminofunctional siloxane.

23. The process of claim 22, wherein the aminofunctional siloxane has the formula

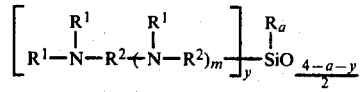

where R is selected from the group consisting of a monovalent hydrocarbon radical having from 1 to 18 carbon atoms and a halogenated monovalent hydrocarbon radical having from 1 to 18 carbon atoms, $R^1$ is selected from the group consisting of hydrogen, monovalent hydrocarbon radicals having from 1 to 30 carbon atoms and monovalent hydrocarbon radicals substituted with hydroxyl groups, $R^2$ is a divalent hydrocarbon radical having from 1 to 20 carbon atoms, a is a number of from 0 to 2, m is an integer of from 0 to 20 and y is a number of from 1 to 4.

* * * * *

UNITED STATES PATENT AND TRADEMARK OFFICE
CERTIFICATE OF CORRECTION

PATENT NO. : 4,644,074

DATED : February 17, 1987

INVENTOR(S) : Paul A. Manis, Eugene R. Martin and Ronald L. Muntz

It is certified that error appears in the above-identified patent and that said Letters Patent is hereby corrected as shown below:

In the claims:

Claim 9, delete "5" and insert --- 6 ---.

Claim 14, delete "5" and insert --- 20 ---.

Claim 15, delete "5" and insert --- 20 ---.

Signed and Sealed this

Twenty-eighth Day of August, 1990

Attest:

HARRY F. MANBECK, JR.

*Attesting Officer*      *Commissioner of Patents and Trademarks*